United States Patent
Davis

(10) Patent No.: US 8,686,851 B2
(45) Date of Patent: Apr. 1, 2014

(54) SYSTEM AND METHOD FOR RAPID LOCATION OF AN ALARM CONDITION

(75) Inventor: Carl Claude Davis, Milwaukee, WI (US)

(73) Assignee: General Electric Company, Schnectady, NY (US)

( * ) Notice: Subject to any disclaimer, the term of this patent is extended or adjusted under 35 U.S.C. 154(b) by 363 days.

(21) Appl. No.: 13/155,503

(22) Filed: Jun. 8, 2011

(65) Prior Publication Data

US 2012/0313775 A1 Dec. 13, 2012

(51) Int. Cl.
*G08B 1/08* (2006.01)
*G08B 23/00* (2006.01)

(52) U.S. Cl.
USPC ............ 340/539.12; 340/539.11; 340/539.13; 340/573.1

(58) Field of Classification Search
USPC ............... 340/539.11, 539.12, 539.16, 573.1, 340/539.13; 345/419, 629, 633; 701/300, 701/533; 705/2, 3; 455/404.2, 466
See application file for complete search history.

(56) References Cited

U.S. PATENT DOCUMENTS

| | | | |
|---|---|---|---|
| 6,064,749 A | 5/2000 | Hirota et al. | |
| 6,124,825 A | 9/2000 | Eschenbach | |
| 6,625,299 B1 | 9/2003 | Meisner et al. | |
| 6,765,569 B2 | 7/2004 | Neumann et al. | |
| 7,127,082 B2 | 10/2006 | Neely | |
| 7,242,306 B2 * | 7/2007 | Wildman et al. | 340/573.1 |
| 7,343,278 B2 | 3/2008 | Billinghurst et al. | |
| 7,450,024 B2 * | 11/2008 | Wildman et al. | 340/669 |
| 7,592,997 B2 | 9/2009 | Evers-Senne et al. | |
| 7,613,356 B2 | 11/2009 | Uchiyama et al. | |
| 7,728,868 B2 | 6/2010 | Razzaque et al. | |
| 8,346,572 B2 * | 1/2013 | Eaton et al. | 705/2 |
| 8,395,498 B2 * | 3/2013 | Gaskill et al. | 340/539.12 |
| 2009/0293012 A1 | 11/2009 | Alter et al. | |
| 2011/0106559 A1 * | 5/2011 | Eaton et al. | 705/3 |
| 2013/0110535 A1 * | 5/2013 | Eaton et al. | 705/2 |
| 2013/0183924 A1 * | 7/2013 | Saigh et al. | 455/404.2 |

* cited by examiner

*Primary Examiner* — Van T. Trieu
(74) *Attorney, Agent, or Firm* — Andrus Intellectual Property Law, LLP

(57) ABSTRACT

A method of notifying a clinician of an alarm condition for a patient including the steps of receiving notice of the alarm condition, identifying a location of the patient, identifying a location of the clinician, calculating guidance information based on the location of the clinician and the location of the patient, and providing the guidance information to a clinician using a portable notification device. The method may further include the steps of identifying a direction and/or an orientation of the clinician, and calculating and displaying the guidance information based on the direction and/or orientation of the clinician.

22 Claims, 5 Drawing Sheets

SYSTEM AND METHOD FOR RAPID LOCATION OF AN ALARM CONDITION

BACKGROUND

Typically, patient monitors include alarm systems that provide audible and/or visual indications of certain predefined conditions—i.e., alarm conditions. For example, some patient monitors include alarms that are triggered based on physiological conditions, such as high or low heart rate thresholds, blood pressure thresholds, arterial oxyhemoglobin saturation, etc. These alarms facilitate supervision of patients and improve patient care by providing caregivers with warnings concerning certain monitored conditions.

Alarm notifications may be auditory and/or visual, and may be local alarms and/or transmitted via a notification system. For example, alarms may be sent to a central management station, such as a nurses' station, either at the time an alarm condition occurs, or after a certain amount of time has passed while the alarm condition remains unacknowledged. Additionally, alarms may be sent to wireless devices, such as pagers, carried by caregivers to give notice of an alarm condition.

In fast-paced healthcare environments, such as an emergency room, a coronary care unit, an intensive care unit, or any other hospital unit, current audible and/or visual indications of alarm conditions can go unnoticed or be difficult to locate. Further, clinicians may be located in the facility remote from the central management station, or otherwise fail to respond to a notice of an alarm condition. In such instances, an alarm condition may not be heeded. Additionally, in patient care units where patients are ambulatory, a patient suffering an alarm condition may be difficult to locate quickly. Time spent trying to locate the patient or determine the nature of the alarm condition extends the response time to the alarm condition and may reduce the overall quality of patient care.

SUMMARY

The present disclosure stems from the inventor's research and development of improved systems and methods for providing clinicians with information to rapidly address alarm conditions within a hospital environment. The inventor has recognized that present alarm notification systems, such as those providing audible and/or visual alarm indicators, may go unnoticed for a time or may be difficult to locate quickly in certain healthcare environments. Thus, the present inventors have recognized that an alarm notification method and system needs to be provided with the ability to rapidly inform clinicians of the location, distance, directions, and nature of patients suffering alarm conditions.

One embodiment relates to a method of notifying a clinician of an alarm condition for a patient comprising the following steps: receiving notice of the alarm condition, identifying a location of the patient, identifying a location of the clinician, calculating guidance information based on the location of the clinician and the location of the patient, and providing the guidance information to the clinician using a portable notification device.

Another embodiment relates to a method of notifying a clinician of an alarm condition using a portable notification device including receiving notice of the alarm condition at the portable notification device, identifying a location of the patient in a healthcare facility, and identifying a position of the clinician in the healthcare facility. The step of identifying the position of the clinician comprises several sub steps, including: identifying the location of the portable notification device, identifying a direction of orientation of the portable notification device, and identifying an angular orientation of the portable notification device. Once the position of the clinician is identified, the method continues by calculating guidance information which includes directions from the current position of the clinician to the location of the patient, and displaying the guidance information on the portable notification device to guide the clinician toward the patient.

Yet another embodiment relates to an alarm notification system comprising a portable notification device that receives notice of an alarm condition, calculates guidance information based on the location of the portable notification device, and then displays the guidance information to the clinician. The portable notification device comprises a receiver that receives notice of an alarm condition for a patient, a location determining means for determining a location of the portable notification device in a healthcare environment, and a display device.

Other principal features and advantages of the invention will become apparent to those skilled in the art upon review of the following drawings, the detailed description, and the appended claims.

DETAILED DESCRIPTION OF THE DRAWINGS

In the present description, certain terms have been used for brevity, clarity and understanding. No unnecessary limitations are to be implied therefrom beyond the requirement of the prior art because such terms are used for descriptive purposes only and are intended to be properly construed. The different systems and methods described herein may be used alone or in combination with other systems and methods. Various equivalents, alternatives, and modifications are possible within the scope of the appended claims. Each limitation of the appended claims is intended to invoke interpretation under 35 USC §112, sixth paragraph, only if the terms "means for" or "steps for" are explicitly recited in the respective limitation.

Figure 1A:
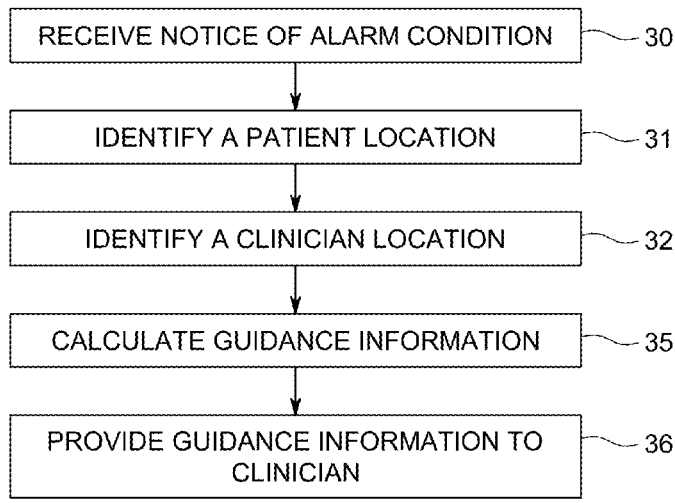
FIGS. 1A and 1B depict flowcharts of the steps performed by a system for rapid location of an alarm condition according to one embodiment.
Figure 2:
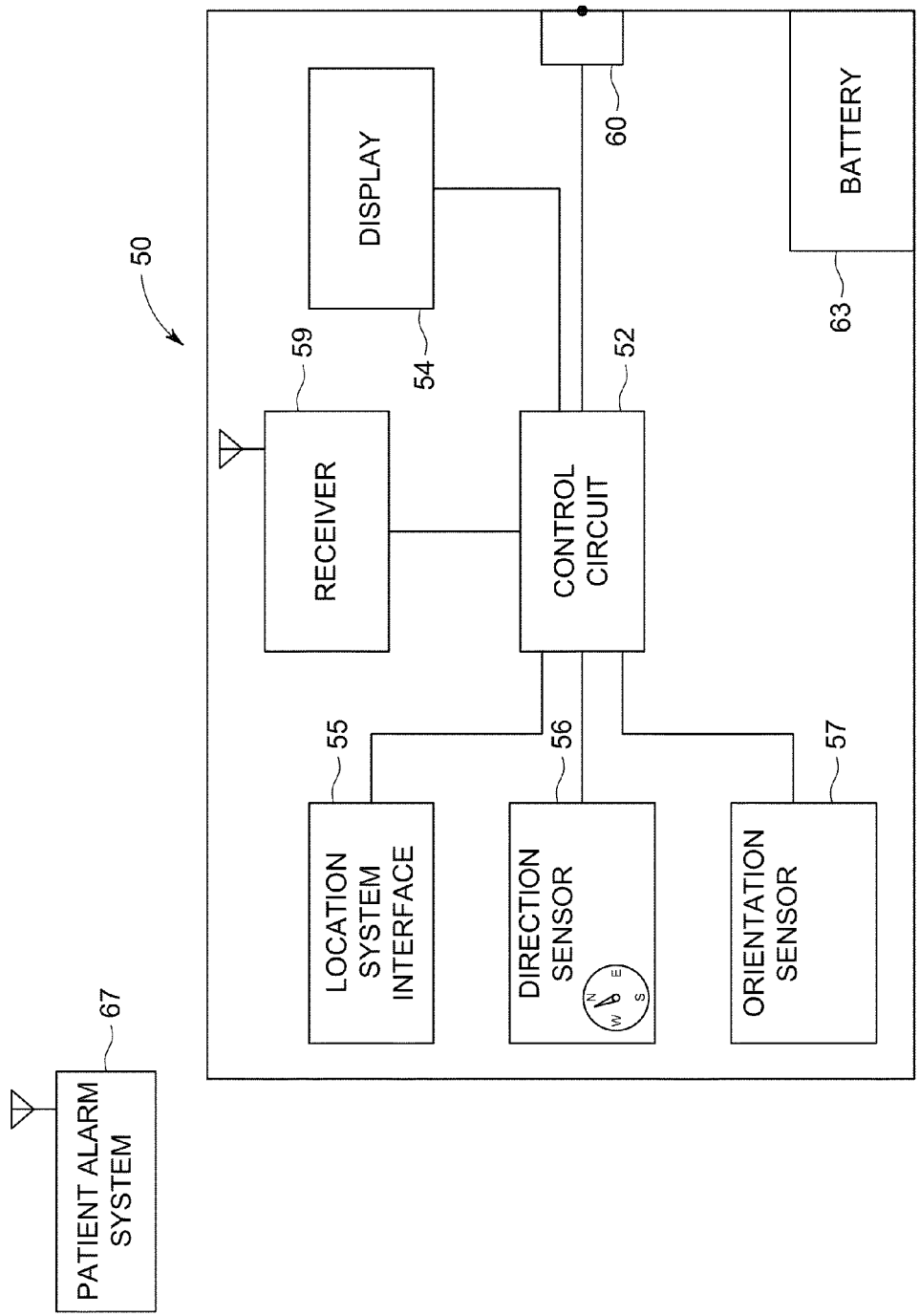
FIG. 2 is a schematic of an embodiment of a system for rapid location of an alarm condition.

Referring to FIG. 1A, a flowchart depicts a method for notifying a clinician of an alarm condition for a patient, which may be performed, for example, by the portable notification device 50 shown in FIG. 2. Initially, notice of an alarm condition is received at block 30. The notice of the alarm condition contains sufficient information such that the existence of a particular alarm condition may be identified. Further, the notice of the alarm condition may contain information that can be used to determine the location of the patient having an alarm condition. Additionally, the notice of the alarm condition may contain information regarding the nature of the alarm condition, such as the patient physiological data that triggered the alarm condition and/or other relevant information regarding the patient's physiology.

Upon receiving notice of an alarm condition 30, the location of the patient having the alarm condition is identified at step 31. Again, information regarding the location of the patient may be received along with the notice of the alarm condition in step 30, or information regarding the location of the patient may be retrieved wirelessly from a separate system, such as a central alarm management system or a patient location tracking system.

At step 32, the location of the clinician that is currently responsible for the care of the patient is identified. When the patient is located on the floor of a hospital, the clinician currently responsible for the care of the patient may be a floor nurse, an on-staff doctor or any other type of medical personnel that is currently responsible for care of the patient that is generating the alarm condition. The step of identifying the location of the clinician 32 may be executed subsequently or simultaneously with the step of identifying the location of the patient 31. The step of identifying the location of the clinician 32 may include utilization of location tracking systems within a hospital environment, such as real-time location services (RTLS) systems (e.g., those utilizing passive or active RFID tags or Wi-Fi tags), wireless medical telemetry service (WMTS) systems, infrared systems, WiFi™ systems, or any wireless system capable of tracking the location of individuals within a hospital environment. Alternatively, the location of the clinician may be identified as step 32 by utilizing the Global Positioning System (GPS).

At step 35, guidance information is calculated based on the information determined at the proceeding steps. At a minimum, guidance information is calculated based on the identification of a patient location, step 31, and the identification of a clinician location, step 32. Guidance information may comprise any information that guides the clinician to the location of the patient suffering an alarm condition. For example, guidance information may comprise step by step audio and/or visual directions from the location of the clinician to the location of the patient. As another example, guidance information may comprise a visual depiction of the location of the patient and/or the clinician on a map. In yet another example, guidance information may comprise depicting a vector connecting the clinician's location and the patient's location.

The guidance information used to guide the clinician to the location of the patient suffering an alarm condition will typically take into account the layout and orientation of the floor on which both the clinician and the patient are located. The guidance information thus will take into account the location of hallways, walls, stairways and room locations to guide the clinician toward the location of the patient suffering an alarm condition.

The guidance information is provided to the clinician at step 36, and may be provided by any means that make the guidance information readily available and immediately accessible by the clinician at the clinician's location. The guidance information may be visual and/or auditory information, and thus may be conveyed via visual or audio devices. For example, the guidance information may be provided on a portable notification device, such as a wearable display device or a handheld display device. In one embodiment, the display is a pair of head-up display (HUD) glasses 10, such as those depicted at FIG. 3. In another embodiment, the display is a hand-held display device.

Figure 1B:
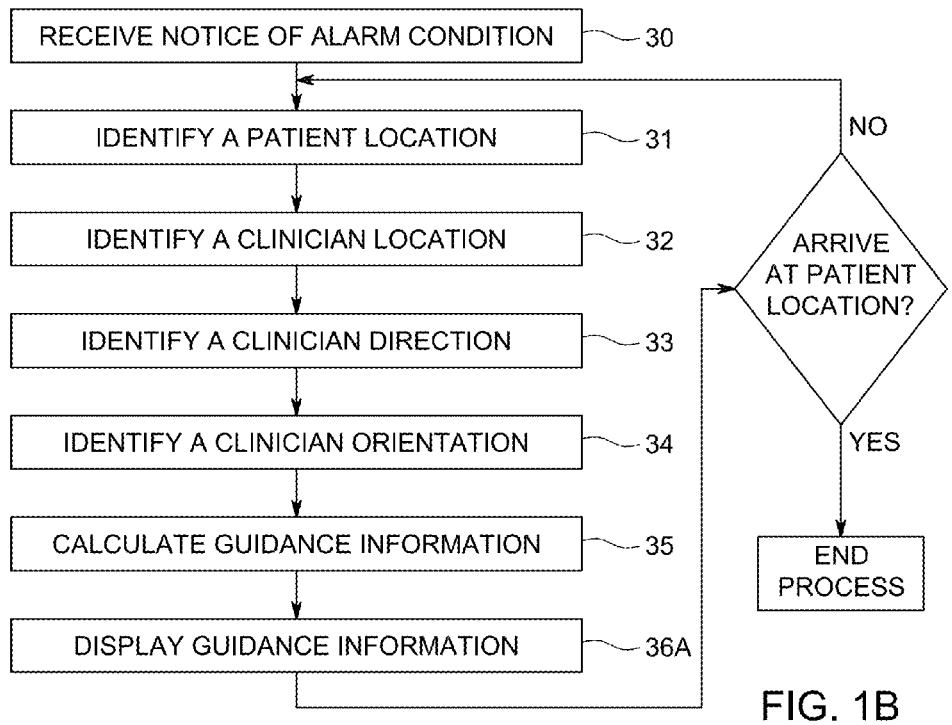

As depicted in FIG. 1B, another embodiment of a method for notifying a clinician of an alarm condition for a patient includes further identifying a direction of a clinician and/or an orientation of a clinician, and includes the direction and/or orientation of the clinician in the calculation of guidance information. In FIG. 1B, steps 30 through 32 proceed as described above. At step 33, the direction of the clinician is identified in 2D space. Identification of the direction of the clinician 33 may be accomplished in any number of ways. In one embodiment, a system implementing the present method may receive input from a direction sensor, such as a compass incorporated into a handheld display device worn or held by the clinician. In such an embodiment, the direction of the clinician may be defined, for example, in polar coordinates with respect to north.

At step 34, the orientation of the clinician is identified. Identification of the orientation of the clinician 34 includes identification of angular orientation in 3-D space, e.g., pitch, yaw, and roll. In an embodiment in which the display device is a pair of glasses, identifying the orientation of the clinician may include the identification of the orientation of the clinician's head or eyes, or it may involve identification of the orientation of a portable notification device, such as a portable notification device 50, worn or held by a clinician. In one embodiment, the step of identifying the orientation of a clinician 34 comprises identifying the orientation of a portable notification device 50 having an orientation sensor that determines and provides the orientation of the device in space. A system implementing the step 34 could use any number of orientation sensors to determine orientation, such as an accelerometer or a gyroscope.

In some embodiments, the step of calculating guidance information at step 35 may include calculations based on the clinician's direction, determined at step 33, and/or the clinician's orientation, determined at step 34. In such embodiments, the guidance information calculated at step 35 may include directions from the location of the clinician to the location of the patient calculated based on the direction and orientation of the clinician determined at step 33. For example, the directions may instruct the clinician to turn right or left, or to turn around, based on the direction that the clinician is currently facing. Likewise, the guidance information may be calculated at step 35 based on the clinician orientation determined at step 34. For example, guidance information may be calculated based on where a clinician is looking, such as in an augmented reality device. In that embodiment, guidance information is calculated to provide directions to the clinician via an augmented reality system such as that depicted in FIGS. 3 and 4 of the present application.

The guidance information may be continually updated as the clinician and/or the patient moves. At step 37 in FIG. 1B, if the clinician has not arrived at the patient location, the process repeats and the patient location, clinician location, etc. are re-identified and the guidance information is recalculated according to the steps described above. At step 37, if the clinician has reached the patient location, the guidance process is terminated. Several methods may be used to determine whether the clinician has arrived at the patient location. For example, it may be determined at step 37 that the clinician has arrived at the patient location if the clinician is within a predefined distance from the patient and is facing in the direction of the patient location. In another embodiment, it may be determined at step 37 that the clinician has arrived at the patient location if the clinician provides input to end the alarm notification process, such as by pressing a button when he or she has located the patient or wishes to terminate the process.

Referring to FIG. 2, a schematic of one embodiment of the portable notification device 50 carried by or worn by the clinician is depicted. The portable notification device 50 has a control circuit 52 which executes the method of notifying a clinician of an alarm condition depicted in FIGS. 1A and 1B and described above. The control circuit is operably connected to a receiver 59 that receives notification of an alarm condition. In some embodiments, the receiver 59 receives notification of an alarm condition from a patient alarm system 67. The patient alarm system 67 may be a central alarm system that is used to monitor multiple monitoring devices for multiple patients. In that embodiment, the central alarm system may send notification of an alarm condition to the portable notification device 50 via the receiver 59. In another embodiment, the patient alarm system 67 may be a single monitoring device connected to one or more patients and capable of detecting an alarm condition and sending a notification of the alarm condition, which is detectable by the receiver 59.

Upon receiving notification of an alarm condition via the receiver 59, the control circuit 52 gathers information from its inputs and calculates status information to lead a clinician to the location of the patient having an alarm condition. The control circuit 52 receives input from the location system interface 55, the direction sensor 56, an orientation sensor 57, and the receiver 59.

The location system interface 55 may be any device or system that allows the portable notification device to determine the location of the clinician by identifying the location of the portable notification device 50. Further, the location system interface 55 may provide the ability to identify the location of an alarming device and/or the patient in a healthcare facility. The location system interface 55 may provide the equivalent of x-y coordinates defined for a particular hospital environment, or it may define a location according to the floor plan of a facility, e.g. room number, floor, unit, etc. Moreover, the system may provide the ability to find the location of an alarming device within a specific hospital floor plan. In that instance, the system may utilize a detailed floor plan to pinpoint the location of the patient and/or the physician and to provide a clinician with contextual directions from the clinician's location to the location of the patient.

In one embodiment, the location system interface 55 may be a passive RFID tag or an active RFID tag, which interfaces with an RFID-based location system installed in a healthcare facility. In another embodiment, the location system interface 55 is a WiFi transceiver or tag that interfaces with a WiFi-based location system. In still another embodiment, the location system may be the Global Positioning System (GPS), and the location system interface 55 may be a GPS receiver. In a GPS embodiment, the location system interface 55 would locate the clinician using GPS coordinates using devices and algorithms that are well known in the art. Further, the portable notification device 50 may also utilize the GPS coordinate location identified by the GPS receiver to identify the location of the clinician within a hospital environment. For example, the location system interface 55 may access a floor plan, or map, of a hospital environment having GPS coordinate markers, and thus may be able to identify the clinician's location within that floor plan.

The direction sensor 56 may be any sensor capable of sensing direction in horizontal 2D space. In one embodiment, the direction sensor 56 is a compass integrated circuit having solid state magnetic sensors. In the embodiment depicted in FIG. 2, the direction sensor 56 is contained in the portable notification device 50. However, in other embodiments the orientation sensor may be separate from the portable notification device 50 while still providing input for the purposes of calculating guidance information. For example, the direction sensor 56 may be provided in a separate device that is connected, either via a wireless or a wired connector, to the portable notification device 50.

The orientation sensor 57 may be any sensor capable of sensing position in 3D space, and may operate independently or in conjunction with the direction sensor 56 to do so. In one embodiment, the step of identifying the orientation of a clinician 34 comprises identifying the orientation of a portable notification device 50 having a multi-access accelerometer integrated circuit that determines and provides the orientation of the device in space. In other embodiments, the portable notification device, such as a portable notification device 50, has a gyroscope as an orientation sensor. In still other embodiments, different sensors or technologies may be used to determine orientation in 3D space.

Depending on the type of orientation sensor used and whether the sensor is capable of independently sensing position within 3D space, the orientation sensor 57 may be used in addition to or in place of a direction sensor 56. Additionally, other embodiments may utilize an orientation sensor 57 which is separate from the portable notification device 50. For example, the step of identifying the direction of the clinician 33 could be executed in a separate device worn by the clinician or attached to or associated with the clinician in some way.

The control circuit 52 calculates guidance information that includes directions from the current location of the clinician to the location of the patient that is generating the alarm condition. The guidance information is calculated based on input from at least the location system interface 55, and in some embodiments based also on input from the direction sensor 56 and/or the orientation sensor 57. The guidance information is then provided to a clinician. The guidance information may be provided to the clinician in a visual manner via the display 54. Additionally or alternatively, the guidance information may be provided to the clinician in an audio form via the audio output 60.

The display 54 may be any type of display capable of providing the guidance information to the clinician. For example, the display may be a wearable display or a handheld display, and it may include any type of display screen—e.g., an LCD screen, an LED screen, a plasma display, etc. Further, the display may be a head-up display (HUD). For example, the HUD may use a projection technique to overlay an image on a transparent medium in a visual field, or it may be a video display in which the user can perceive their environment by means of a live video capture with images superimposed on the displayed video. An embodiment involving a HUD is illustrated and discussed herein at FIGS. 3 and 4.

The portable notification device 50 depicted in FIG. 2 also has an audio output 60 which is operatively connected to the control circuit 52 and which can be used to output audible guidance information to a clinician. The audible guidance information provided via the audio output 60 can be provided in place of or in addition to guidance information provided via the display 54. The audible guidance information may comprise auditory directions guiding a clinician to the location of the patient. For example, the audible guidance information may include directions in language form—e.g., turn right at the next hallway—or directions in the form of sounds which communicate direction—e.g., a clicking in the right ear at increasing speed as the clinician approaches the place at which a right turn should be made.

The portable notification device 50 may also include a battery 63. The battery 63 is preferably a rechargeable battery that powers the device 50. The battery 63 may also be configured to be removable and/or interchangeable.

The portable notification device 50 may further interface with other devices and/or systems, such as patient monitoring devices and/or systems, electronic medical record databases, tracking and information systems operating in a healthcare facility, etc.

Figure 3:
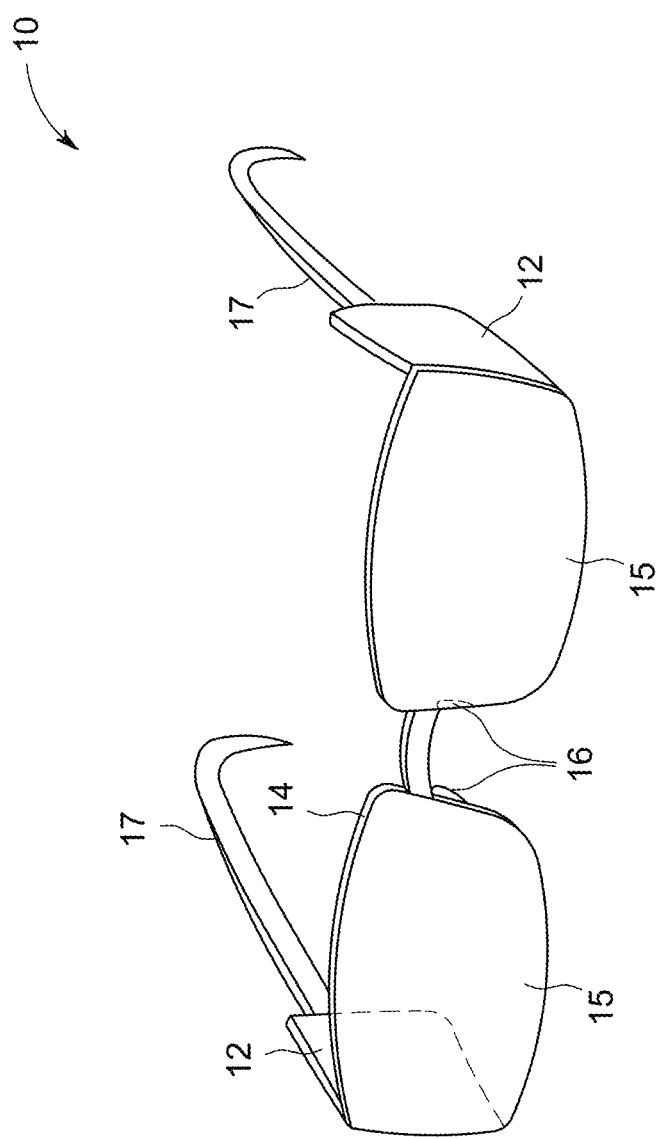
FIG. 3 depicts an exemplary embodiment of an augmented reality system for rapid location of an alarm condition.
Figure 4:
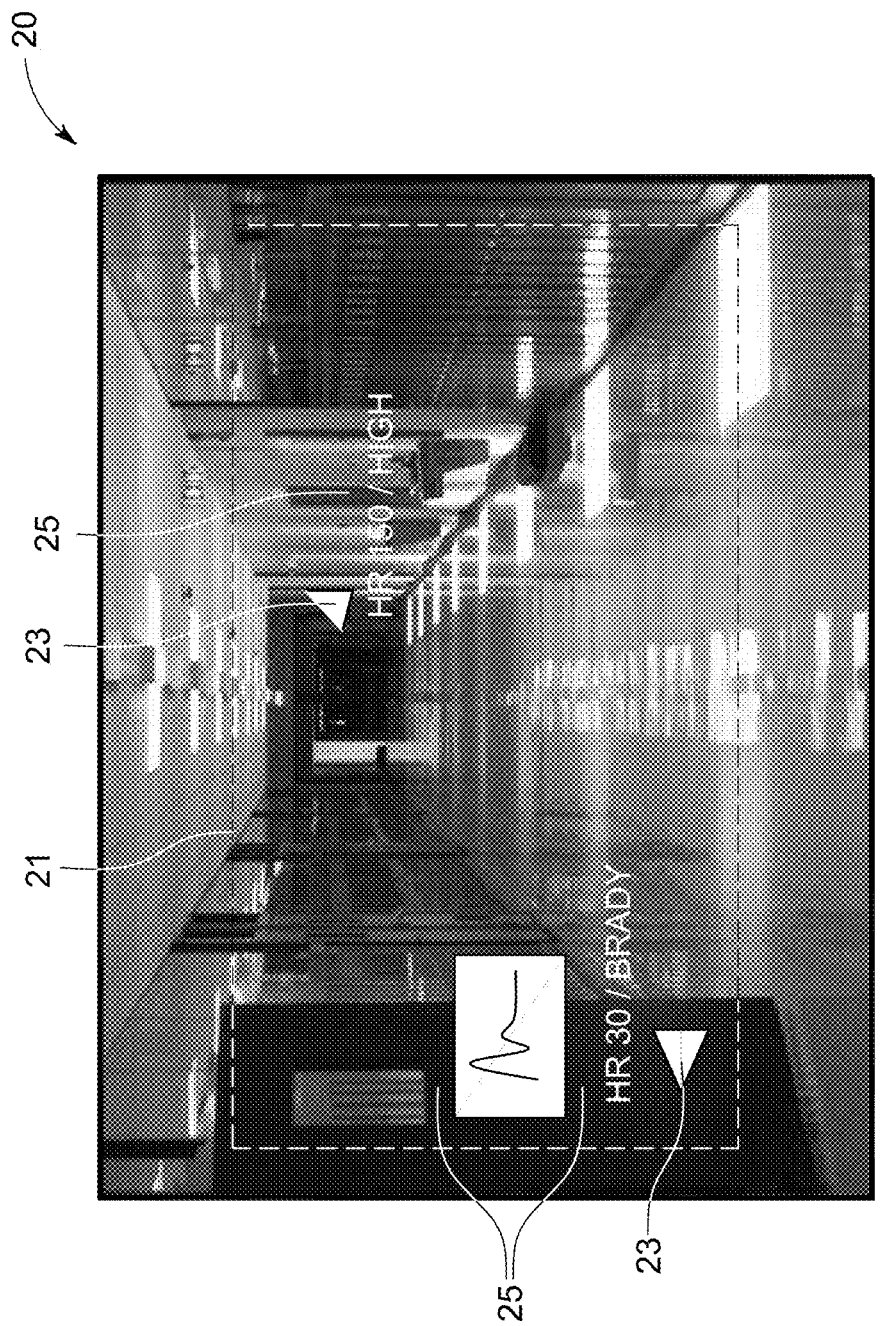
FIG. 4 is an exemplary illustration of an augmented reality display in a system for rapid location of an alarm condition.

FIG. 3 depicts one embodiment of a portable notification device 50 which is a set of HUD glasses 10. The HUD glasses 10 may be worn by a clinician as if they were a regular pair of glasses. The lenses 15 of the HUD glasses 10 are transparent, allowing the user to see his or her surroundings naturally and without impediment. In one embodiment, the HUD glasses 10 convey guidance information to a user by overlaying or projecting computer generated images over the user's view of his or her surroundings. Thus, the HUD glasses provide an augmented reality display for the user comprised of the user's real world surroundings augmented by computer generated images. An example of the augmented reality display from a user's perspective is illustrated at FIG. 4.

Referring still to FIG. 3, the HUD glasses 10 have many of the same features found on regular glasses, including a frame 14 having an ear piece 17 and a nose support 16. However, unlike standard eye glasses, the HUD glasses 10 contain at least one image projection node 12 which generates and projects guidance information onto the adjacent lens 15. Any display technology appropriate for head-up display devices may be implemented. In one embodiment, the image projection node 12 has a small projector configured to project images onto the lens 15 of the HUD glasses in a way that the image is incorporated into the visual field of a user wearing the HUD glasses. For example, the projector may use LEDs or lasers as a source of illumination. In such an embodiment, the lens 15 provides the surface onto which the information is projected for view.

The lenses 15 can be concave or flat, and may have a special coating that reflects the light projected onto it from the projector while allowing all other wavelengths of light to pass through. Alternatively, the lenses 15 may capture the image from the projector using refraction. In another embodiment, the image projection node 12, in combination with the lens or lenses 15, may implement optical waveguide technology to produce images directly in the lens 15.

The image projection node 12 may contain some or all of the components of the portable notification device 50 depicted in FIG. 2. In one embodiment, all components of the portable notification device including the location system interface 55, the direction sensor 56, the orientation sensor 57, the receiver 59, the control circuit 52, and the battery 63—are contained in at least one image projection node 12 on the HUD glasses 10. Incorporating the direction sensor 56 and the orientation sensor 57 embedded in at least one image projection node 12 yields the benefit of providing information regarding the direction and orientation of the user's head. In that embodiment, the guidance information can be displayed at the correct position relative to the user's field of view, even as the user moves his or her head. In such an embodiment, an algorithmic calculation is performed by the control circuit using information gathered from its inputs to define where a clinician is "looking" in 3-D space, to calculate that orientation with respect to the location of the patient, and to generate and project an image onto the lens or lenses 15 providing guidance information.

The guidance information may be projected onto one or both of the lenses 15 of the HUD glasses 10. While many of the components of the portable notification device 50 may be located in one image projection node 12 on one side of the HUD glasses 10, the guidance information may still be projected onto both lenses 15. In one embodiment, the HUD glasses 10 contain an image projection node 12 on both the right and left sides of the glasses. Each of the location system interface 55, the direction sensor 56, the orientation sensor 57, and the control circuit 52 are contained in one of the right or left image projection nodes 12. Additionally, wires or buses may run through the frame 14 of the HUD glasses 10 to connect the devices contained in each of the right and left image projection nodes 12. Also, the battery 63 may be housed in one of the right or left image projection nodes 12 and may be connected through the frame 14 to power devices contained in both image projection nodes 12.

An audio output may exist on one or both sides of the HUD glasses 10. The audio output may be a speaker or it may connect to an earpiece to be placed in the user's ear. The audio output may be used to supply guidance information or other information to the clinician, and may supplement or augment the visual information provided. For example, the audio output could provide audio instructions recorded from another clinician attending to the patient, or from a central alarm station manager.

In another embodiment, the portable notification device 50 may be a pair of glasses having an LED guidance display. The glasses may contain LEDs appearing in the user's field of view and providing guidance information. For example, the glasses may contain a line of LED's across the top or bottom that could light up in such a way as to indicate a vector to the location of a patient and/or provide the clinician with directional indicators guiding him or her to the location of the patient. In another example, the LED's could display a description of the location of the patient (e.g. room 1102, bathroom) and/or list directions on how to locate the patient based on the location of the clinician.

In yet another embodiment, the portable notification device 50 may be a handheld display device. The handheld display device may display the guidance information in connection with a video display of the surrounding environment. For example, the display may be a virtual reality display wherein a user can to perceive his or her environment by means of a live video capture with guidance information and images superimposed on the displayed video. In such an embodiment, the control circuit 52 would utilize input from the location system interface 55, along with the direction sensor 56 and/or the orientation sensor 57 to calculate and display the guidance information with respect to the video capture. Thus, as the portable notification device 50 is moved, the guidance information is updated to correspond to the video captured by the device.

Referring now to FIG. 4, an exemplary view on a virtual reality embodiment of a portable notification device 50, such as through a pair of HUD glasses 10, is depicted. The display area 21 appears within the user's field of view 20 and contains images projected onto the lens 15, which overlay the user's field of view 20. The images appearing in display area 21 include guidance information for locating a patient having an alarm condition. The guidance information may appear as a direction indicator 23 pointing in the direction of the location of the patient having an alarm condition. In the depicted embodiment, an arrow is used as the direction indicator 23 to indicate the direction of the patient having the alarm condition. Alternatively, the direction indicator 23 may be step-by-step directions for locating a patient having an alarm condition. Or, the direction indicator 23 could be lines appearing on the screen visually marking a path leading towards a patient. As the clinician's head moves, the direction indicator 23 is adjusted to track the physical surroundings such that the guidance information is displayed correctly with respect to the user's field of view 20.

In addition to the direction indicators 23, the guidance information displayed in the display area may include physiologic data 25 for a patient suffering an alarm condition, which may provide details of the alarm criticality, parametrics, and waveform information for the alarm, or any other information relevant to the clinician's understanding or treatment of the patient suffering the alarm condition. Such information may also allow a physician to immediately assess the severity of an alarm and prioritize response accordingly. For example, if multiple alarm conditions are occurring at the same time, the physiological data displayed may help a clinician prioritize which patient or patient(s) must be attended to first.

Moreover, the portable notification device 50, including embodiments involving HUD glasses 10, may provide additional information when patient care is being provided. In one embodiment, when a clinician encounters one of his or her patients, such as when he or she enters a patient's room, the display on a portable notification device 50 may include important information necessary for the care of the patient. Further, orientation and positional information provided by the system could be combined with image recognition and tracking software or systems to provide context-aware information. For example, when looking at the patient through the HUD glasses 10, physiological data or information could be overlayed to match the appropriate location on the patient—e.g., EEG near the patient's head, heart rate and ECG over the patient's chest, etc.

Figure 5:
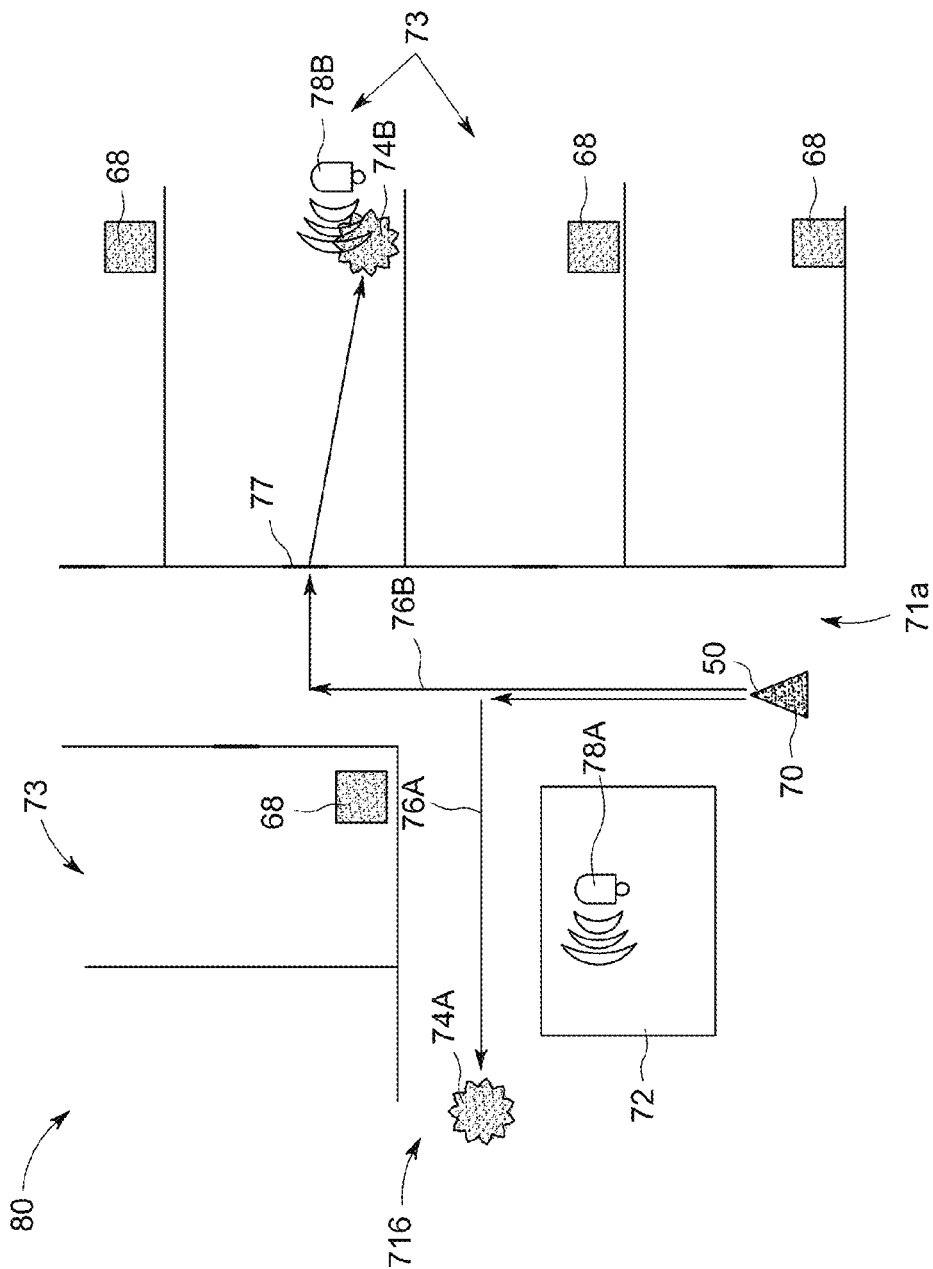
FIG. 5 depicts an exemplary hospital environment employing an embodiment of a system and method for rapid location of an alarm condition.

FIG. 5 demonstrates an exemplary healthcare facility 80, such as a hospital, wherein the portable notification device 50 is implemented by a clinician 70. Further, FIG. 5 demonstrates some of the challenges clinicians face when locating a patient having an alarm condition. In the embodiment of FIG. 5, the clinician 70 is standing in a hallway 71*a* when two different patients experience alarm conditions 74*a* and 74*b*. One patient experiencing an alarm condition, 74*a*, is ambulatory and is in the adjacent hallway 71*b*. A second patient experiencing an alarm condition, 74*b*, is inside a patient room 73 that includes a patient monitor 68. The clinician 70 hears audible alarms 78*a* and 78*b* for the two patients 74*a* and 74*b*, respectively. For the ambulatory patient 74*a*, the alarm is indicated at the central nurses' station 72. For patient 74*b*, the audible alarm 78*b* is a local alarm generated by the patient monitor 68 at the patient's bedside.

In the exemplary situation, the clinician 70 has no immediate or reliable indication of the location of either patient 74*a* or 74*b*. To obtain the location of patient 74*a* without the portable notification device 50, the clinician 70 must first go to the central nurses' station 72. For the patient experiencing the alarm condition 74*b*, the audible alarm 78*b* emanates from the patient room 73. In this situation, without the portable notification device 50, the clinician 70 is without any immediate and precise indication of the locations of the patient suffering an alarm condition 74*a* and 74*b*. From this illustration, it should be evident that it is possible to misidentify the locations of the audible alarms or to be confused as to the direction of the sound emanating from the audible alarm, especially when multiple alarms are sounding simultaneously.

In the exemplary hospital environment 80 depicted in FIG. 5, where the clinician 70 has a portable notification device 50, the clinician is given immediate guidance information 76 to the location of the patient suffering alarm conditions 74*a* and 74*b*. Thus, through the use of the portable notification device 50, the clinician 70 is able to quickly locate the relevant patients without first visiting the central nurses' station 72 or going through trial and error to identify the patient room 73 in which the alarm condition is occurring.

The portable notification device 50 calculates guidance information as a path 76*a* from the location of the clinician 70 to the location of a patient suffering an alarm condition 74*a*. Likewise, the portable notification device 50 calculates guidance information as path 76*b*, guiding the clinician through the door 77 of the correct room and to the patient 74*b*. The portable notification device 50 provides the guidance information to the clinician 70 so that the clinician 70 can take immediate action and not lose time trying to locate the relevant patients.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A method of notifying a clinician of an alarm condition for a patient, the method comprising:
   receiving notice of the alarm condition and alarm information regarding the nature of the alarm condition;
   identifying a location of the patient;
   identifying a location of the clinician;
   calculating guidance information based on the location of the clinician and the location of the patient; and
   providing the guidance information and the alarm information to the clinician using a portable notification device.

2. The method of claim 1, wherein the portable notification device is a wearable display device worn on a users' head and providing guidance information within the user's field of view.

3. The method of claim 2, wherein the wearable display device is glasses with a head up display.

4. The method of claim 2, wherein the wearable display devices is an augmented reality display utilizing at least one arrow to indicate the guidance information, and wherein the augmented reality display is updated to account for movement of the wearable display device.

5. The method of claim 1, wherein the portable notification device is a handheld display device.

6. The method of claim 1, wherein the portable notification device is includes an auditory notification device presenting auditory guidance information.

7. The method of claim 1, wherein the step of calculating guidance information is further based on a floor plan of a healthcare facility.

8. The method of claim 7, wherein the step of calculating guidance information comprises calculating directions from the location of the clinician to the location of the patient.

9. The method of claim 1, wherein the step of identifying the location of the clinician includes identifying the location of the portable notification device utilizing a location tracking system within a healthcare facility.

10. The method of claim 1, further including identifying a direction of the portable notification device based on input from a direction sensor in the portable notification device, and wherein the step of calculating guidance information further includes calculating guidance information based on the direction of the portable notification device.

11. The method of claim 1, further including the step of identifying an orientation of the portable notification device based on input from an orientation sensor in the portable notification device, and wherein the step of calculating guidance information further includes calculating guidance information based on the orientation of the portable notification device.

12. The method of claim 1, wherein the step of providing the guidance information using the portable notification device further includes providing physiologic information of the patient using the portable notification device.

13. The method of claim 1, further including the steps of:
receiving notice of a second alarm condition and second alarm information regarding the nature of the second alarm condition;
identifying a second location of a patient associated with the second alarm condition;
identifying an updated location of the clinician;
calculating guidance information based on the updated location of the clinician and the second location of the patient associated with the second alarm condition; and
providing the guidance information and the second alarm information using the portable notification device such that the clinician is able to determine which alarm condition is a higher priority.

14. A method of notifying a clinician of an alarm condition for a patient using a portable notification device, the method comprising:
receiving notice of the alarm condition at the portable notification device;
identifying a location of the patient in a healthcare facility;
identifying a position of the clinician in the healthcare facility, wherein identifying the position of the clinician comprises:
identifying the location of the portable notification device;
identifying a direction of the portable notification device; and
identifying an orientation of the portable notification device;
calculating guidance information, based on the location of the patient and the position of the clinician;
displaying the guidance information on the portable notification device;
identifying an updated position of the clinician in the healthcare facility as the clinician moves toward the patient; and
calculating updated guidance information based on the updated position of the clinician; and
displaying the updated guidance information on the portable notification device.

15. The method of claim 14, wherein the portable notification device is a head-up display device providing guidance information overlaid on the clinician's field-of-view.

16. The method of claim 14, wherein the portable notification device is a handheld display device.

17. The method of claim 14, wherein the step of calculating a path from the clinician to the patient includes computing a path based on the floor plan of the healthcare facility.

18. An alarm notification system comprising:
a portable notification device comprising:
a receiver that receives notice of an alarm condition for a patient;
a location determining means for determining a location of the portable notification device in a healthcare environment;
an orientation determining means for determining an orientation of the portable notification device in the healthcare environment and
an augmented reality display;
wherein, upon receiving notice of an alarm condition at the receiver, the portable notification device calculates guidance information based on the layout of the healthcare environment compared to the location and the orientation of the portable notification device; and
displays guidance information using the augmented reality display.

19. The system of claim 18, wherein the portable notification device further includes a direction sensor that determines a direction of the portable notification device;
and wherein the portable notification device calculates the guidance information based on the direction of the portable notification device.

20. The system of claim 18, wherein the portable notification device further calculates updated guidance information based on an updated location of the portable notification device and displays the updated guidance information.

21. The system of claim 18, wherein the augmented reality display is a head-up display providing guidance information in the form of at least one arrow overlaid on a user's field of view.

22. The system of claim 18, wherein the receiver receives alarm information indicating the nature or severity of the alarm condition, and the augmented reality display displays the alarm information.

* * * * *